(12) United States Patent
Faig et al.

(10) Patent No.: US 12,064,504 B2
(45) Date of Patent: *Aug. 20, 2024

(54) COSMETIC COMPOSITIONS COMPRISING HIGH AMOUNTS OF TRIFLUOROMETHYLHENYL VALYLGLYCINE

(71) Applicant: L'OREAL, Paris (FR)

(72) Inventors: Jonathan James Faig, Sayreville, NJ (US); Yon Jae Yoon, Roselle, NJ (US); Susan Halpern Chirch, Basking Ridge, NJ (US); Angelike Galdi, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/050,526

(22) Filed: Oct. 28, 2022

(65) Prior Publication Data

US 2023/0133621 A1 May 4, 2023

Related U.S. Application Data

(60) Provisional application No. 63/273,965, filed on Oct. 31, 2021.

(51) Int. Cl.
| | |
|---|---|
| *A61K 8/00* | (2006.01) |
| *A61K 8/21* | (2006.01) |
| *A61K 8/34* | (2006.01) |
| *A61K 8/81* | (2006.01) |
| *A61K 8/92* | (2006.01) |
| *A61Q 19/00* | (2006.01) |

(52) U.S. Cl.
CPC .............. *A61K 8/8141* (2013.01); *A61K 8/21* (2013.01); *A61K 8/342* (2013.01); *A61K 8/922* (2013.01); *A61Q 19/00* (2013.01)

(58) Field of Classification Search
CPC . A61K 8/44; A61K 8/062; A61K 8/37; A61K 8/604; A61K 8/8158; A61K 8/8182
See application file for complete search history.

(56) References Cited

U.S. PATENT DOCUMENTS

| | | | |
|---|---|---|---|
| 10,449,133 B1 * | 10/2019 | Faig | ............... A61K 8/34 |
| 10,898,496 B2 | 1/2021 | Simard | |
| 10,973,749 B2 | 4/2021 | Sverdlove et al. | |
| 11,058,614 B2 | 7/2021 | Choi et al. | |
| 2002/0019547 A1 | 2/2002 | Tuloup et al. | |
| 2002/0058010 A1 | 5/2002 | Picard-Lesboueyries et al. | |
| 2002/0182238 A1 | 12/2002 | Creton | |
| 2002/0197289 A1 | 12/2002 | Chevalier et al. | |
| 2003/0215413 A1 | 11/2003 | Fares et al. | |
| 2004/0137024 A1 | 7/2004 | Abriat et al. | |
| 2004/0162272 A1 | 8/2004 | Hansenne et al. | |
| 2005/0191337 A1 | 9/2005 | Gueret | |
| 2006/0026775 A1 | 2/2006 | Rozot et al. | |
| 2007/0015840 A1 | 1/2007 | Dalko et al. | |
| 2007/0202065 A1 | 8/2007 | Devin-Baudoin et al. | |
| 2007/0202203 A1 | 8/2007 | Amar | |
| 2007/0248633 A1 | 10/2007 | Baldo | |
| 2008/0050333 A1 | 2/2008 | Lemoine et al. | |
| 2008/0131391 A1 | 6/2008 | Ellington et al. | |
| 2008/0153839 A1 | 6/2008 | Cotton et al. | |
| 2008/0159970 A1 | 7/2008 | Willemin | |
| 2008/0226756 A1 | 9/2008 | Willemin et al. | |
| 2008/0293962 A1 | 11/2008 | Dalko et al. | |
| 2009/0016971 A1 | 1/2009 | Gaudry et al. | |
| 2009/0016974 A1 | 1/2009 | Pruche et al. | |
| 2009/0018200 A1 | 1/2009 | Willemin et al. | |
| 2009/0041691 A1 | 2/2009 | Candau et al. | |
| 2009/0285868 A1 | 11/2009 | Richard et al. | |
| 2009/0317430 A1 | 12/2009 | Cassin et al. | |
| 2010/0086502 A1 | 4/2010 | Lucet-Levannier et al. | |
| 2010/0112100 A1 | 5/2010 | Willemin et al. | |
| 2010/0189675 A1 | 7/2010 | Pelletier | |
| 2010/0197805 A1 | 8/2010 | Cassin | |
| 2011/0021438 A1 | 1/2011 | Dalko et al. | |
| 2011/0130704 A1 | 6/2011 | Baldo et al. | |
| 2013/0259912 A1 | 10/2013 | Suzuki et al. | |
| 2013/0344015 A1 | 12/2013 | Gaudry et al. | |

(Continued)

FOREIGN PATENT DOCUMENTS

| | | |
|---|---|---|
| DE | 102017201050 A1 | 7/2018 |
| EP | 3082974 A1 | 10/2016 |

(Continued)

OTHER PUBLICATIONS

"Beiersdorf Personalizes Face Care with Launch of New Brand O.W.N." Newsroom-Press Releases, 2021, pp. 1-2.

(Continued)

*Primary Examiner* — Isaac Shomer
*Assistant Examiner* — Bryan James Rego
(74) *Attorney, Agent, or Firm* — POLSINELLI PC

(57) ABSTRACT

The present disclosure relates to stable cosmetic compositions containing high amounts of acetyl trifluoromethylphenyl valylglycine. The cosmetic compositions further include high amounts of hydroxypropyl tetrahydropyrantriol, taurate copolymers, fatty alcohols, fatty compounds (other than the fatty alcohols), nonionic emulsifiers, and water. Methods for stabilizing cosmetic compositions containing high amounts of acetyl trifluoromethylphenyl valylglycine and methods for treating the skin with the cosmetic compositions is also described.

20 Claims, No Drawings

(56) References Cited

U.S. PATENT DOCUMENTS

| | | |
|---|---|---|
| 2014/0287005 A1 | 9/2014 | Chevalier et al. |
| 2015/0047664 A1 | 2/2015 | Samain et al. |
| 2015/0157539 A1 | 6/2015 | Shimizu et al. |
| 2015/0174047 A1 | 6/2015 | Chiou et al. |
| 2015/0174050 A1 | 6/2015 | Lu et al. |
| 2015/0265504 A1* | 9/2015 | Crane ............... A61Q 1/10 424/63 |
| 2016/0213599 A1 | 7/2016 | Devie |
| 2016/0220308 A1 | 8/2016 | Khormaei et al. |
| 2016/0220804 A1 | 8/2016 | Khormaei et al. |
| 2017/0151538 A1 | 6/2017 | Balooch et al. |
| 2017/0154372 A1 | 6/2017 | Balooch et al. |
| 2017/0326045 A1 | 11/2017 | Lorant et al. |
| 2017/0348221 A1 | 12/2017 | Maruyama et al. |
| 2018/0085721 A1 | 3/2018 | Rinaldis et al. |
| 2018/0243182 A1 | 8/2018 | Ricard et al. |
| 2018/0344609 A1* | 12/2018 | Lu .................. A61K 8/062 |
| 2019/0038539 A1 | 2/2019 | Garruto et al. |
| 2019/0110967 A1 | 4/2019 | Chiou |
| 2019/0159980 A1* | 5/2019 | Chen .................. A61Q 19/02 |
| 2020/0211078 A1 | 7/2020 | Balooch et al. |
| 2020/0246228 A1 | 8/2020 | Maczkiewitz et al. |
| 2020/0253853 A1 | 8/2020 | Lu et al. |
| 2020/0277093 A1 | 9/2020 | Besen et al. |
| 2021/0015719 A1 | 1/2021 | Lu et al. |

FOREIGN PATENT DOCUMENTS

| | | |
|---|---|---|
| FR | 3059545 A1 | 6/2018 |
| WO | 2011030308 A1 | 3/2011 |
| WO | 2021180400 A1 | 9/2021 |

OTHER PUBLICATIONS

Kacey Culliney, "Beiersdorf files patent on AI skin profiling and product recommendation method," 2021, pp. 1-3.
Preliminary Search Report issued on Nov. 11, 2022 for corresponding French Application No. FR 2200825.
Database GNPD [Online]; Mintel Anonymous: "Serum Absolute Advanced Age-Reversing Makeup," 2016 XP055969756.
Database GNPD [Online]; Mintel Anonymous: "Personalised Anti-Aging Care [Integral Care] + [Marine Collagen Booster]," 2021 XP055969412.
Database GNPD [Online]; Mintel Anonymous: "Anti-Wrinkle Concentrate," 2008 XP055631674.

* cited by examiner

COSMETIC COMPOSITIONS COMPRISING HIGH AMOUNTS OF TRIFLUOROMETHYLHENYL VALYLGLYCINE

CROSS-REFERENCE TO RELATED APPLICATIONS

This application claims benefit of U.S. Ser. No. 63/273,965 filed Oct. 31, 2021, and benefit of French Application No. FR 2200825, filed on Jan. 31, 2022, which are incorporated herein by reference in their entirety.

FIELD OF THE INVENTION

The instant disclosure relates to stable cosmetic compositions that include high amounts of acetyl trifluoromethylphenyl valylglycine; and to methods for stabilizing cosmetic compositions containing high amounts of acetyl trifluoromethylphenyl valylglycine. The instant disclosure also describes methods for treating skin with the cosmetic compositions.

SUMMARY

In an aspect, the present disclosure is directed to, among other things, cosmetic compositions including a surprisingly high amount of acetyl trifluoromethylphenyl valylglycine. Acetyl trifluoromethylphenyl valylglycine provides a myriad of cosmetic benefits to the skin but is very difficult to incorporate high amounts of acetyl trifluoromethylphenyl valylglycine into cosmetic compositions and retain stability. The inventors of the instant disclosure developed, among other things, surprisingly stable compositions that include high amounts of acetyl trifluoromethylphenyl valylglycine. Due to the high amounts of acetyl trifluoromethylphenyl valylglycine, the cosmetic compositions provide exceptional cosmetic properties to the skin, for example, improving elasticity, promoting the production of hyaluronic acid, synthesis of collagen, synthesis of epidermal structural components, regeneration of damaged tissue, and reducing the effects of aging of skin of the face or body.

In an aspect, the present disclosure is directed to, among other things, a cosmetic composition in the form of an oil in water emulsion, preferably a gel emulsion. In an embodiment, the cosmetic composition includes:
 (a) acetyl trifluoromethylphenyl valylglycine;
 (b) hydroxypropyl tetrahydropyrantriol;
 (c) two or more taurate copolymers;
 (d) one or more fatty alcohols;
 (e) one or more fatty compounds;
 (f) one or more nonionic emulsifiers; and
 (g) water;
 wherein all percentages by weight are based on the total weight of the cosmetic composition.

Nonlimiting examples of taurate copolymers include acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof.

Nonlimiting examples of fatty alcohols include those chosen from $C_6$-$C_{20}$ fatty alcohols, for example, decyl alcohol, undecyl alcohol, dodecyl alcohol, myristyl alcohol, cetyl alcohol, stearyl alcohol, isostearyl alcohol, isocetyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof.

Nonlimiting examples of fatty compounds include fatty esters (such as isononyl isononanoate), polyolefins (such as petrolatum), waxes, squalane, squalene, hydrogenated polyisobutene, hydrogenated polydecene, polybutene, mineral oil, pentahydrosqualene, plant and/or vegetable oil, hydrocarbon-based oils (such as isohexadecane), and a mixture thereof.

Nonlimiting examples of nonionic emulsifiers include alkanolamides, sorbitan fatty esters (such as sorbitan isostearate and sorbitan oleate), ethoxylated sorbitan fatty esters (such as polysorbate 80), polyol esters, glyceryl esters, polyglucosides (such as ceteraryl glucoside), glycerol ethers, oxyethylenated ethers, oxypropylenated ethers, and ethylene glycol polymers.

Nonlimiting examples of water-soluble solvents include glycerin, mono-alcohols, polyols (such as polyhydric alcohols), glycols, and a mixture thereof.

Nonlimiting examples of skin active agents include madecassoside, a moisturizing agent, a depigmenting agent, an anti-wrinkle agent, a skin active agent for oily skin, an antioxidant, a flavonoid, a vitamin, a skin whitening agent, and a mixture thereof.

Silicones can optionally be included in the cosmetic compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, the cosmetic compositions of the instant case can be free or essentially free from dimethicones, amomdimethicones, dimethiconols, cyclosiloxanes, siloxanes, etc.

In an embodiment, the cosmetic compositions form part of a kit comprising a cosmetic composition according to the instant disclosure and one or more separately contained compositions. In an embodiment, the compositions are received in a device, for example, a device that dispenses the cosmetic composition and the one or more separately contained compositions. In an embodiment, the device dispenses the cosmetic composition and the one or more separately contained compositions without mixing them together prior to dispensing. Even though high amounts of acetyl trifluoromethylphenyl valylglycine are incorporated into the cosmetic compositions, the compositions are unique in that they are compatible with other cosmetic compositions, in particular, other cosmetic compositions for treating the skin.

Another aspect of the instant disclosure relates to methods for stabilizing high amounts of acetyl trifluoromethylphenyl valylglycine into cosmetic compositions. These methods, as describe throughout the disclosure, and comprise incorporating the high amounts of acetyl trifluoromethylphenyl valylglycine into the compositions of the instant disclosure.

Another aspect of the instant disclosure relates to methods for treating skin. The methods include applying the cosmetic composition according to the instant disclosure to the skin. In an embodiment, the methods improve elasticity, promote the production of hyaluronic acid, synthesis of collagen, synthesis of epidermal structural components, regeneration of damaged tissue, and reduce the effects of aging of the skin of the face or body. In certain embodiments the methods include reinforcing or improving the natural lipid barrier of the skin; treating dry and/or aging skin; maintaining and/or improving moisture balance of skin; and/or improving the overall appearance of skin.

Other features and iterations of the invention are described in more detail

DETAILED DESCRIPTION

A common problem associated with formulating compositions, especially composition comprising multiple components, is ensuring physical stability, chemical stability, solubility, and the like. Many additives for food, cosmetics, personal care, and household products into which they are incorporated are difficult to stabilize and solubilize, especially when used in high amounts. The consequence of stability and solubility problems is significant. For example, stability problems can cause partial, if not complete, loss of product integrity, color loss, malodor, viscosity changes, etc. Stability and solubility problems can also cause an increased or a decreased amount of the component in question to be applied. With respect to active ingredients, stability and solubility problems reduce or eliminate activity, and prevent the active ingredients from reaching their intended target in the desired amount.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively influence the skin, causing dryness, rash, and puffiness.

Human skin acts as a primary barrier between the body and its environment. Crucial for this skin barrier function is the lipid matrix in the outermost layer of the skin (epidermis), the stratum corneum (SC). Two of its functions are (1) to prevent excessive water loss through the epidermis and (2) to avoid that compounds from the environment permeate into the viable epidermal and dermal layers and thereby provoke an immune response. The composition of the SC lipid matrix is dominated by three lipid classes: cholesterol, free fatty acids, and ceramides. These lipids adopt a highly ordered, 3-dimensional structure of stacked densely packed lipid layers (lipid lamellae): the lateral and lamellar lipid organization. The way in which these lipids are ordered depends on the composition of the lipids. One very common skin disease in which the SC lipid barrier is affected is atopic dermatitis (AD).

What is needed, among other things, are compositions which include high amounts of acetyl trifluoromethylphenyl valylglycine that reinforce or improve the natural lipid barrier of the skin, treat dry and/or aging skin; maintain and/or improve moisture balance of skin; and/or improve the overall appearance of skin, and the like.

In an aspect, the present disclosure is directed to, among other things, a stable cosmetic composition that includes high amounts of acetyl trifluoromethylphenyl valylglycine and to methods for stabilizing cosmetic compositions containing high amounts of acetyl trifluoromethylphenyl valylglycine. In an embodiment, the compositions include:

(a) about 1 to about 5 wt. % of acetyl trifluoromethylphenyl valylglycine;
(b) about 10 to about 40 wt. % of hydroxypropyl tetrahydropyrantriol;
(c) about 2 to about 15 wt. % of two or more taurate copolymers;
(d) about 0.5 to about 10 wt. % of one or more fatty alcohols;
(e) about 5 to about 25 wt. % of one or more fatty compounds;
(f) about 0.1 to about 10 wt. % of one or more nonionic emulsifiers; and
(g) water;
wherein the composition is an oil in water emulsion, preferably a gel emulsion, and all percentages by weight are based on the total weight of the cosmetic composition.

A gel emulsion is an oil in water emulsion, wherein the aqueous phase is a gel and the oil droplets/particulates are dispersed throughout the gel matrix.

(a) Acetyl Trifluoromethylphenyl Valylglycine

Although it imparts a multitude of beneficial properties to skin, acetyl trifluoromethylphenyl valylglycine is difficult to solubilize and therefore difficult to formulate into stable cosmetic compositions. It tends to crystalize out of formulations. The cosmetic compositions of the instant disclosure allow for high amounts of acetyl trifluoromethylphenyl valylglycine to be solubilized and stabilized, e.g., the compositions carry high amounts of acetyl trifluoromethylphenyl valylglycine and prevent the acetyl trifluoromethylphenyl valylglycine from crystallizing.

The amount of the acetyl trifluoromethylphenyl valylglycine will vary but in various embodiment is from about 1 to about 5 wt. %, based on the total weight of the cosmetic composition. In various embodiments, the amount of the acetyl trifluoromethylphenyl valylglycine is from about 1.5 to about 5 wt. %, about 2 to about 5 wt. %, about 2.5 to about 5 wt. %, about 1 to about 4 wt. %, about 1.5 to about 4 wt. %, about 2 to about 4 wt. %, about 2.5 to about 4 wt. %, or about 3 wt. %, based on the total weight of the cosmetic compositions. In another embodiment, the total amount of acetyl trifluoromethylphenyl valylglycine is from about 2.6 to about 3.4 wt. %, based on the total weight of the cosmetic composition.

(b) Hydroxypropyl Tetrahydropyrantriol

Hydroxypropyl tetrahydropyrantriol is a sugar-protein hybrid made from xylose and can effectively activate the synthesis of GAGs (glycosamineoglycans), promote the production of hyaluronic acid, synthesis of collagen, adhesion between the dermis and the epidermis, the synthesis of epidermal structural components, the regeneration of damaged tissue, and maintain skin elasticity.

The amount of hydroxypropyl tetrapyrantriol in the cosmetic compositions will vary but in various embodiment is from about 10 wt. % to about 40 wt. %, based on the total weight of the composition. In various embodiments, the amount of hydroxypropyl tetrapyrantriol in the composition is from about 10 wt. % to about 35 wt. %, from about 10 to about 30 wt. %, from about 10 to about 25 wt. %, from about 10 to about 20 wt. %, about 12 to about 35 wt. %, about 12 to about 30 wt. %, about 12 to about 25 wt. %, about 12 to about 20 wt. %, from about 12 to about 18 wt. %, from about 14 to about 30 wt. %, from about 14 to about 25 wt. %, from about 14 to about 20 wt. %, or from about 14 to about 18 wt. %, based on the total weight of the composition.

(c) Taurate Copolymers

The cosmetic composition of the instant disclosure include two or more taurate copolymers. These copolymers can act as gelling agents, thickeners, and provide emulsification properties. In particular, the inventors discovered that taurate copolymers are particularly effective for stabilizing the cosmetic compositions of the instant disclosure. Furthermore, in certain embodiments, it is preferable that at least one of the taurate copolymers functions, at least in part, as a polymeric emulsifier and at least one of the taurate copolymers functions, at least in part, as a viscosity enhancing/gelling agent.

In a particularly preferred embodiment at least one of the two or more taurate copolymers is chosen from taurate copolymers that function as polymeric emulsifiers, in particular, chosen from hydroxyethyl acrylate/sodium acryloyl dimethyl taurate copolymer, ammonium acryloyldimethyltaurate/steareth-25 methacrylate crosspolymer, ammonium acryloyldimethyltaurate/beheneth-25 methacrylate crosspolymer, and mixtures thereof.

Nonlimiting examples taurate copolymers include acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof The taurate copolymers may be hydrophilic and may contain an acrylate component. The at least one taurate copolymer may include, for example, acrylamide/sodium acryloyl dimethyl taurate copolymer, hydroxyethyl acrylate/sodium acryloyl dimethyl taurate copolymer, and/or sodium acrylate/sodium acryloyl dimethyl taurate copolymer. In some instances, at least one taurate copolymer is obtainable from ethylenically unsaturated, sulpho-functional monomers and ethylenically unsaturated hydrophilic monomers, for example from crosslinked anionic copolymers of acrylamide or methacrylamide and of 2-acrylamido-2-methyl-propanesulfonic acid.

The total amount of the two or more taurate copolymers will vary but in various embodiment the total amount of the two or more taurate copolymers is from about 2 wt. % to about 15 wt. % based on the total weight of the cosmetic composition. In further embodiments, the amount of the two or more taurate copolymers in the cosmetic composition is from about 2 to about 12 wt. %, about 2 to about 10 wt. %, about 2 to about 8 wt. %, about 2 to about 5 wt. %, about 2 to about 4 wt. %, about 2 to about 3 wt. %, about 2.5 to about 15 wt. %, about 2.5 to about 12 wt. %, about 2.5 to about 10 wt. %, about 2.5 to about 8 wt. %, about 2.5 to about 5 wt. %, or about 2.5 to about 4 wt. %, based on the total weight of the cosmetic composition.

In a preferred embodiment, each of the individual taurate copolymers included in the two or more taurate copolymers of cosmetic compositions is in a minimum amount of at least 0.7 wt. %, preferably at least 0.8 wt. %, based on the total weight of the cosmetic composition. In other words, none of the individual taurate copolymers is present in an amount of less than 0.7 wt. %, based on the total weight of the cosmetic composition. Therefore, in various embodiments, the total amount of the two or more taurate copolymers in the cosmetic composition is from about 2 wt. % to about 15 wt. % based on the total weight of the cosmetic composition, provided that each individual taurate copolymer of the two or more taurate copolymers is in an amount of at least 0.7 wt. %, preferably at least 0.8 wt. %, based on the total weight of the cosmetic composition.

In further embodiments, the amount of the two or more taurate copolymers in the cosmetic composition is from about 2 to about 12 wt. %, about 2 to about 10 wt. %, about 2 to about 8 wt. %, about 2 to about 5 wt. %, about 2 to about 4 wt. %, about 2 to about 3 wt. %, about 2.5 to about 15 wt. %, about 2.5 to about 12 wt. %, about 2.5 to about 10 wt. %, about 2.5 to about 8 wt. %, about 2.5 to about 5 wt. %, or about 2.5 to about 4 wt. %, based on the total weight of the cosmetic composition, provided that each individual taurate copolymer of the two or more taurate copolymers is in an amount of at least 0.7 wt. %, preferably at least 0.8 wt. %, based on the total weight of the cosmetic composition.

In certain embodiments, it is preferable that the cosmetic composition includes three or more taurate copolymers. In particular, it is useful to include three or more taurate copolymers chosen from acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof. More preferably, is it useful to use three or more taurate copolymers comprising ammonium acryloyldimethyl taurate/VP copolymer, acrylamide/sodium acryloyl dimethyl taurate copolymer, and hydroxyethyl acrylate/sodium acryloyldimethyl taurate copolymer. In a particularly preferred embodiment, these three taurate copolymers are included in the following amounts, based on the total weight of the cosmetic compositions:

0.1 to 4 wt. %, preferably 0.5 to 3 wt. %, more preferably 0.6 to 2 wt. % of ammonium acryloyldimethyl taurate/VP copolymer, 0.7 to 4 wt. %, preferably 0.7 to 3 wt. %, more preferably, 0.8 to 2 wt. % of acrylamide/sodium acryloyl dimethyl taurate copolymer, and 0.1 to about 4 wt. %, preferably 0.5 to 3 wt. %, more preferably 0.6 to 2 wt. % of hydroxyethyl acrylate/sodium acryloyldimethyl taurate copolymer.

In a preferred embodiment, the cosmetic composition comprises:

0.6 to 2 wt. % of ammonium acryloyldimethyl taurate/VP copolymer, 0.8 to 2 wt. % of acrylamide/sodium acryloyl dimethyl taurate copolymer, and 0.6 to 2 wt. % of hydroxyethyl acrylate/sodium acryloyldimethyl taurate copolymer.

(d) Fatty Alcohols

The cosmetic composition of the instant disclosure includes one or more fatty alcohols. The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the cosmetic compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Non-limiting examples of useful fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol), and mixtures thereof.

In certain embodiments, the one or more fatty alcohols have from 12 to 24 carbon atoms. Specific nonlimiting examples include cetyl alcohol, stearyl alcohol, cetearyl alcohol, behenyl alcohol, lauryl alcohol, myristic or myristyl alcohol, arachidyl alcohol, lignoceryl alcohol, or mixtures thereof.

Preferably, the cosmetic composition includes one or more solid fatty alcohol, for example, chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C=C double bond) and contain from 12 to 40 carbon atoms.

The liquid fatty alcohols may be represented by: R—OH, wherein R denotes a C12-C24 branched alkyl group or an alkenyl group (comprising at least one C12-C24 double bond C=C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, cosmetic compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the cosmetic compositions preferably include stearyl alcohol.

The total amount of the one or more fatty alcohols in the cosmetic compositions will vary but in various embodiment is from about 0.5 wt. % to about 10 wt. %, based on the total weight of the composition. In various embodiments, the amount of one or more fatty alcohols is from about 0.5 to about 8 wt. %, about 0.5 to about 5 wt. % 0.5 to about 4 wt. %, about 0.5 to about 3 wt. %, about 1 to about 10 wt. %, about 1 to about 8 wt. %, about 1 to about 5 wt. %, about 1 to about 4 wt. %, about 1 wt. % to about 3 wt. %, about 1.5 to about 10 wt. %, about 1.5 to about 8 wt. %, about 1.5 to about 5 wt. %, about 1.5 to about 4 wt. %, about 1.5 to about 3 wt. %, based on the total weight of the composition.

(e) Fatty Compounds

The term "fatty compounds" is interchangeable with the "fatty materials." Fatty compounds are known as compounds that are not soluble (or only sparingly soluble) in water; they are hydrophilic and are often solubilized in organic solvents. They include materials such as oils, fats, waxes, hydrocarbons, fatty esters, etc. For purposes of the instant disclosure, "fatty compounds" do not include fatty acids, which are separately referred to above. In addition, silicones are not considered fatty compounds according to the instant disclosure. Non-limiting examples of useful fatty compounds include oils, waxes, alkanes (paraffins), fatty acids, fatty esters, triglyceride compounds, lanolin, hydrocarbons, derivatives thereof, and mixtures thereof. Fatty compounds are described by the International Federation Societies of Cosmetic Chemists, for example, in Cosmetic Raw Material Analysis and Quality, *Volume I: Hydrocarbons, Glycerides, Waxes and Other Esters* (Redwood Books, 1994), which is incorporated herein by reference in its entirety.

Non-limiting examples of fatty compounds include oils, mineral oil, alkanes (paraffins), fatty acids, fatty alcohol derivatives, fatty acid derivatives, esters of fatty alcohols, hydroxy-substituted fatty acids, waxes, triglyceride compounds, lanolin, and a mixture thereof.

Fatty Alcohol Derivatives

The fatty compounds may include one or more fatty alcohol derivatives, which are different from fatty alcohols (component (d)). Fatty alcohol derivatives include fatty esters derived from one or more fatty alcohols. Fatty alcohol derivatives also include alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acids

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

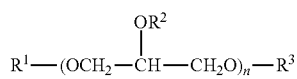

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Waxes

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (Helianthus annuus), carnauba, candelilla, ouricury or japan wax or cork fibre or sugarcane waxes), or a mixture thereof.

Oils

In some instances, the fatty compounds may include or be chosen from one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelargan-ate; and triesters, such as glyceryl trioctanoate. Non-limiting examples of oils that may, optionally, be included in the cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

In some embodiments, the cosmetic composition may include one or more fatty compounds chosen from fatty esters (such as isononyl isononanoate), polyolefins (such as petrolatum), waxes, squalane, squalene, hydrogenated polyisobutene, hydrogenated polydecene, polybutene, mineral oil, pentahydrosqualene, plant and/or vegetable oil, hydrocarbon-based oils (such as isohexadecane), or a mixture thereof.

The amount of the one or more fatty compounds in the cosmetic compositions will vary but in various embodiment is from about 2 wt. % to about 25 wt. %, based on the total weight of the cosmetic composition. In various embodiments, the amount of the one or more fatty compounds is from about 2 to about 20 wt. %, about 2 to about 15 wt. %, about 2 to about 12 wt. %, about 3 to about 20 wt. %, about 3 to about 15 wt. %, about 3 to about 12 wt. %, about 5 to about 20 wt. %, about 5 to about 15 wt. %, about 5 to about 12 wt. %, about 6 to about 15 wt. %, or about 6 to about 12 wt. %, based on the total weight of the cosmetic composition.

(f) Nonionic Emulsifiers

The cosmetic composition of the instant disclosure comprises one or more nonionic emulsifiers. Nonlimiting examples of nonionic emulsifiers include ethoxylated sorbitan fatty esters (such as polysorbate 80), polyol esters, glyceryl esters, alkyl polyglucosides (such as ceteraryl glucoside), glycerol ethers, oxyethylenated ethers, oxypropylenated ethers, and ethylene glycol polymers. In addition, the nonionic emulsifiers may be chosen from alkyl polyglucosides; alcohols, alpha-diols, alkylphenols and esters of fatty acids, being ethoxylated, propoxylated or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof.

The nonionic emulsifiers may be chosen from alcohols and alpha-diols, these compounds being polyethoxylated and/or polypropoxylated and/or polyglycerolated, the number of ethylene oxide and/or propylene oxide groups possibly ranging from 2 to 100, and the number of glycerol groups possibly ranging from 2 to 30; these compounds comprising at least one fatty chain comprising from 8 to 30 carbon atoms and especially from 16 to 30 carbon atoms.

Mention is also be made of polyethoxylated fatty amides preferably having from 2 to 30 ethylene oxide units, polyglycerolated fatty amides including on average from 1 to 5, and in particular from 1.5 to 4, glycerol groups; polyoxyethylenated fatty acid esters of sorbitan having preferably from 2 to 40 units of ethylene oxide, fatty acid esters of sucrose, polyoxyalkylenated and preferably polyoxyethylenated fatty acid esters containing from 2 to 150 mol of ethylene oxide, such as oxyethylenated plant oils.

Useful nonionic surfactants include those of the alkyl (poly)glycoside type, represented especially by the following general formula: $R_1O—(R_2O)_t-(G)_v$, in which: $R_1$ represents a linear or branched alkyl or alkenyl substituent comprising 6 to 24 carbon atoms and especially 8 to 18 carbon atoms, or an alkylphenyl substituent whose linear or branched alkyl substituent comprises 6 to 24 carbon atoms and especially 8 to 18 carbon atoms; $R_2$ represents an alkylene substituent comprising 2 to 4 carbon atoms; G represents a sugar unit comprising 5 to 6 carbon atoms; t denotes a value ranging from 0 to 10 and preferably 0 to 4; and v denotes a value ranging from 1 to 15 and preferably 1 to 4. Preferably, the alkyl(poly)glycoside surfactants are compounds of the formula described above in which: $R_1$ denotes a linear or branched, saturated or unsaturated alkyl substituent comprising from 8 to 18 carbon atoms; $R_2$ represents an alkylene substituent comprising 2 to 4 carbon atoms; t denotes a value ranging from 0 to 3 and preferably equal to 0; and G denotes glucose, fructose or galactose, preferably glucose; the degree of polymerization, i.e. the value of v, possibly ranging from 1 to 15 and preferably from 1 to 4; the mean degree of polymerization more particularly being between 1 and 2. The glucoside bonds between the sugar units are generally of 1-6 or 1-4 type and preferably of 1-4 type. In particular, the alkyl(poly)glycoside surfactant may be an alkyl(poly)glucoside surfactant $C_8/C_{16}$alkyl (poly)glucosides 1,4, and in particular decyl glucosides and caprylyl/capryl glucosides.

Useful nonionic surfactants may be chosen from polyoxyethylenated C8-C30 fatty acid esters (preferably C12-C18) of sorbitan, polyethoxylated C8-C30 (preferably C12-18) fatty alcohols, polyglycerolated C8-C30 (preferably C12-C18) fatty acid esters, polyoxyethylenated compounds having preferably from 2 to 30 moles of ethylene oxide, polyglycerolated compounds having preferably from 2 to 16 moles of glycerol; and mixtures thereof.

The polyoxyethylenated C8-C30 fatty alcohols may be chosen from C12-C18 fatty alcohols, in particular polyoxyethylenated lauryl alcohol, cetyl alcohol, myristyl alcohol, and stearyl alcohol having from 2 to 30 mol of ethylene oxide, such as: cetyl alcohol polyoxyethylenated with 6 EO (Ceteth-6) (HLB 11.1) cetyl alcohol polyoxyethylenated with 10 EO (Ceteth-10) (HLB 12.9) cetyl alcohol polyoxyethylenated with 20 EO (Ceteth-20) (HLB 15.7) cetyl alcohol polyoxyethylenated with 24 EO (Ceteth-24) (HLB 16.3 lauryl alcohol polyoxyethylenated with 4 EO (Laureth-4) (HLB 9.4) lauryl alcohol polyoxyethylenated with 7 EO (Laureth-7) (HLB 12.3) lauryl alcohol polyoxyethylenated with 9 EO (Laureth-9) (HLB 13.6) lauryl alcohol polyoxyethylenated with 10 EO (Laureth-10) (HLB 13.9) lauryl alcohol polyoxyethylenated with 12 EO (Laureth-12) (HLB 14.6) lauryl alcohol polyoxyethylenated with 21 EO (Laureth-21) (HLB 15.5) lauryl alcohol polyoxyethylenated with 23 EO (Laureth-23) (HLB 16.3) stearyl alcohol polyoxyethylenated with 2 EO (Steareth-2) (HLB 4.9) stearyl alcohol polyoxyethylenated with 10 EO (Steareth-10) (HLB 12.4) stearyl alcohol polyoxyethylenated with 20 EO (Steareth-20) (HLB 15.2) stearyl alcohol polyoxyethylenated with 21 EO (Steareth-21) (HLB 15.5)

The polyoxyethylenated C8-C30 fatty acid esters (preferably C12-C18) of sorbitan may be chosen from polyoxyethylenated esters of C12-C18 fatty acids, in particular lauric, myristic, cetylic or stearic acids, of sorbitan especially containing from 2 to 30 mol of ethylene oxide, such as: polyoxyethylenated sorbitan monolaurate (4 EO) (Polysorbate-21) (HLB 13.3) polyoxyethylenated sorbitan monolaurate (20 EO) (Polysorbate-20) (HLB 16.7) polyoxyethylenated sorbitan monopalmitate (20 EO) (Polysorbate-40) (HLB 15.6) polyoxyethylenated sorbitan monostearate (20 EO) (Polysorbate-60) (HLB 14.9) polyoxyethylenated sorbitan monostearate (4 EO) (Polysorbate-61) (HLB 9.6) polyoxyethylenated sorbitan monooleate (20 EO) (Polysorbate-80) (HLB 15).

In a preferred embodiment, the cosmetic compositions include one or more nonionic surfactants chosen from polyoxyethylenated C8-C30 fatty acid esters (preferably C12-C18) of sorbitan, preferably polyoxyethylenated esters of C12-C18 fatty acids.

The polyglycerolated C8-C30 fatty acid esters, which are particularly preferred, may be chosen from polyglycerolated esters of C12-C18 fatty acids, in particular lauric, myristic, palmitic, stearic or isostearic acid, having from 2 to 16 mol of glycerol, such as: polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof.

In some embodiments, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids mention is made of glyceryl stearate (glyceryl mono-, di- and/or tristearate) (CTFA name: glyceryl stearate) or glyceryl ricinoleate and mixtures thereof.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Alkyl polyglucosides are a class of useful nonionic surfactants. Non-limiting examples of alkyl polyglucosides include alkyl polyglucosides having the following formula:

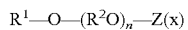

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides include lauryl glucoside, octyl glucoside, decyl glucoside, coca glucoside, sucrose laurate, caprylyl/capryl glucoside, and sodium lauryl glucose carboxylate, and mixtures thereof. Typically, the at least one alkyl poly glucoside compound is selected from the group consisting of lauryl glucoside, decyl glucoside and coca glucoside, and more typically lauryl glucoside. In some instances, decyl glucoside is particularly preferred.

Polyglycerol-Based Emulsifiers

Polyglycerol-based emulsifiers are a useful type of nonionic emulsifiers. Nonlimiting examples include polyglyceryl 10-stearate, polyglyceryl-3-caprate, polyglyceryl-3-diisostearate, polyglyceryl-3 methylglucose distearate, or a mixture thereof. More generally, the polyglycerol-based emulsifiers may be polyglycerol esters of fatty acids having a structure in accordance with the following formula:

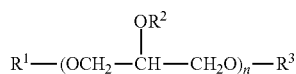

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

In certain embodiments, the polyglycerol-based emulsifier may be chosen from polyglyceryl esters of C12-22 saturated, unsaturated and branched chain fatty acids, such as polyglyceryl-4 isostearate, polyglyceryl-3 oleate, polyglyceryl sesquioleate, triglyceryl diisostearate, diglyceryl monooleate, tetraglyceryl monooleate, and mixtures thereof. Non-limiting examples of glyceryl esters can include glyceryl caprylate, glyceryl caprate, glyceryl cocoate, glyceryl laurate, and combinations thereof.

Nonlimiting examples of polyglycerolated fatty acid esters include polyglyceryl-10 laurate; polyglyceryl-10 myristate; polyglyceryl-2 palmitate, polyglyceryl-3 palmitate, polyglyceryl-6 palmitate, polyglyceryl-10 palmitate, polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof. In some instances, polyglyceryl-2 isostearate is particularly useful.

In a preferred embodiment, the one or more nonionic emulsifiers are chosen from sorbitan fatty esters (e.g., sorbitan isostearate and sorbitan oleate), ethoxylated sorbitan fatty esters (e.g., polysorbate-80), polyol esters, glyceryl esters, polyglucosides (e.g., cetearyl glucoside), and mixtures thereof The total amount of the one or more nonionic emulsifiers in the cosmetic compositions will vary but in various embodiment is from about 0.1 wt. % to about 10 wt. %, based on the total weight of the cosmetic composition. In further embodiments, the total amount of the one or more nonionic emulsifiers in the cosmetic composition is from about 0.1 to about 8 wt. %, from about 0.1 to about 5 wt. %, from about 0.1 to about 3 wt. %, about 0.2 to about 10 wt. %, about 0.2 to about 8 wt. %, about 0.2 to about 5 wt. %, about 0.2 to about 3 wt. %, about 0.3 to about 10 wt. %, about 0.3 to about 8 wt. %, about 0.3 to about 5 wt. %, or about 0.3 to about 3 wt. %, 0.5 to about 10 wt. %, about 0.5 to about 8 wt. %, about 0.5 to about 5 wt. %, or about 0.5 to about 3 wt. %, 1.0 to about 10 wt. %, about 1.0 to about 8 wt. %, about 1.0 to about 5 wt. %, or about 1.0 to about 3 wt. %, based on the total weight of the cosmetic composition.

(g) Water

The amount of water in the cosmetic compositions can and will vary depending on the amount of the other components in the cosmetic compositions. Nonetheless, in various embodiments, the amount of water is from about 35 wt. % to about 85 wt. %. In further embodiments, the amount of the water is from about 35 to about 80 wt. %, about 35 to about 75 wt. %, about 35 to about 70 wt. %, about 40 to about 85 wt. %, about 40 to about 80 wt. %, about 40 to about 75 wt. %, about 40 to about 70 wt. %, about 50 to about 85 wt. %, about 50 to about 80 wt. %, about 50 to about 75 wt. %, about 50 to about 70 wt. %, based on the total weight of the cosmetic composition.

(h) Water-Soluble Solvents

The cosmetic composition of the instant disclosure may include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvents have a solubility of at least 60%, 70%, 80%, or 90%. Non-limiting examples of water-soluble solvents include, for example, glycerin, alcohols (for example $C_{1-10}$ or $C_{1-4}$ alcohols), organic solvents, polyols, glycols, and a mixture thereof.

Nonlimiting examples of water-soluble solvents include monoalcohols and polyols such as ethyl alcohol, isopropyl alcohol, propyl alcohol, isopropyl alcohol, benzyl alcohol, 4-tert-butylcyclohexanol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are also useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some instances, the cosmetic compositions of the instant disclosure include one or more glycols and/or one or more alcohols, for example, one or more water-soluble solvents selected from the group consisting of propylene glycol, butylene glycol, capryloyl glycol, propanediol, glycerin, and a mixture thereof.

The total amount of the one or more water-soluble solvents will vary but in various embodiment is from about 0.1 to about 20 wt. %, based on the total weight of the cosmetic composition. In further embodiments, the total amount of the one or more water-soluble solvents is from about 0.1 to about 15 wt. %, about 0.1 to about 10 wt. %, about 0.5 to about 20 wt. %, about 0.5 to about 15 wt. %, about 0.5 to about 10 wt. %, about 1 to about 20 wt. %, about 1 to about 15 wt. %, about 1 to about 10 wt. %, based on the total weight of the cosmetic composition.

(i) Thickening Polymers

In certain embodiments, the cosmetic compositions of the instant disclosure may optionally include one more thickening polymer(s), which are different from the two or more taurate copolymers (c). Non-limiting examples of various types of thickening polymers include polyacrylate, polymethacrylate, polyethylacrylate, polyacrylamide, poly C10-30 alkyl acrylate, acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer, carbomers, hydrophobically modified polypolyacrylates; hydrophobically modified polyacrylic acids, hydrophobically modified polyacrylamides; hydrophobically modified polyethers wherein these materials may have a hydrophobe that can be selected from cetyl, stearyl, oleayl, and combinations thereof, acrylamide/ammonium acrylate copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyimide-3, polyquaternium-37, sodium polyacrylate, and a mixture thereof.

Among the nonionic thickening polymers that may be mentioned are:

(1) Celluloses modified with groups comprising at least one fatty chain; examples that may be mentioned include: hydroxyethylcelluloses modified with groups comprising at least one fatty chain, such as alkyl, arylalkyl or alkylaryl groups, or mixtures thereof, and in which the alkyl groups are preferably C8-C22, for instance the product NATROSOL PLUS GRADE 330 CS (C16 alkyls) sold by the company Aqualon, or the product BERMOCOLL EHM 100 sold by the company Berol Nobel; and hydroxyethylcelluloses modified with alkylphenyl polyalkylene glycol ether groups, such as the product AMERCELL POLYMER HM-1500 (polyethylene glycol (15) nonylphenyl ether) sold by the company Amerchol, (2) Hydroxypropyl guars modified with groups comprising at least one fatty chain, such as the product ESA-FLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc, (3) Copolymers of vinylpyrrolidone and of fatty-chain hydrophobic monomers; examples that may be mentioned include: the products ANTARON V216 or GANEX V216 (vinylpyrrolidone/hexadecene copolymer) sold by the company I.S.P. the products ANTARON V220 or GANEX V220 (vinylpyrrolidone/ eicosene copolymer) sold by the company I.S.P., (4) Copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name ANTIL 208, (5) Copolymers of hydrophilic methacrylates or acrylates and of hydrophobic monomers comprising at least one fatty chain, for instance the polyethylene glycol methacrylate/lauryl methacrylate copolymer, (6) Polyurethane polyethers comprising in their chain both hydrophilic blocks usually of polyoxyethylenated nature and hydrophobic blocks, which may be aliphatic sequences alone and/or cycloaliphatic and/or aromatic sequences.

In a particularly preferred embodiment, the one or more thickening polymers includes a polymer of the ester of acrylic acid and C10-30 alcohol, e.g., poly C10-30 alkyl acrylate.

The amount of the one or more thickening polymer(s), when present, will vary but in various embodiments is from about 0.01 to about 5 wt. %, based on the total weight of the composition. In further embodiments, the total amount of the one or more thickening polymer(s) is from about 0.01 to about 4 wt. %, about 0.01 to about 3 wt. %, about 0.1 to about 5 wt. %, about 0.1 to about 4 wt. %, about 0.1 to about 3 wt. %, about 0.5 to about 5 wt. %, about 0.5 to about 4 wt. %, or about 0.5 to about 3 wt. %, based on the total weight of the composition.

(j) Miscellaneous Ingredients

The cosmetic compositions of the instant disclosure may optionally include one or more miscellaneous ingredients. Miscellaneous ingredients are ingredients that are compatible with the cosmetic compositions and do not disrupt or materially affect the basic and novel properties of the cosmetic compositions. Miscellaneous ingredients commonly used in cosmetics are known in the art. Non-limiting examples include miscellaneous emulsifiers/surfactants other than the nonionic emulsifiers of (f), preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, etc. In a preferred embodiment, the cosmetic compositions of the instant disclosure include one or more skin active agents, in particular, madecassoside. Nonlimiting examples of various miscellaneous ingredients that may optionally be include (or excluded) from the cosmetic compositions is provided below.

Miscellaneous Emulsifiers/Surfactants

Miscellaneous emulsifiers/surfactants may optionally be included in the cosmetic compositions. Miscellaneous emulsifiers/surfactants are those that are not the nonionic emulsifiers of (f). The miscellaneous emulsifiers/surfactants may be nonionic, anionic, cationic, and/or amphoteric/zwitterionic.

Antioxidants

Examples of antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ.-tocotrienol, d-delta-tocotrienol) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, emblica officinalis, and bioflavonoids from rose hip and citrus may be used including water soluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids can also function as antioxidants. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosm in, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcum in, bis-Desmethoxycurcum in, Tetrahydrocurcum in, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Skin Active Agents

Nonlimiting examples of skin active agents include madecassoside, retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate; —derivatives particularly copper and copper pidolate as Cuivridone Solabia—extracts from plants of *Arnica montana, Cinchona succirubra, Eugenia caryophyllata, Humulus lupulus, Hypericum perforatum, Mentha* pipenta 25 *Rosmarinus officinalis, Salvia officinalis* and *Thymus vulgaris*, all marketed for example by Maruzen—extracts of meadowsweet (*Spiraea* ulmaria), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—*Phellodendron* extracts such as those sold under the name *Phellodendron* extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of *Terminalia chebula*, nasturtium and of bioavailable zinc (microalgae), such as that sold under the name Seborilys Green Tech; —extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed laminaria extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by sociateLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *Cinchona* bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

In a preferred embodiment, the cosmetic compositions of the instant disclosure include one or more skin active agents, for example, madecassoside. Similarly, in certain embodiments, the cosmetic compositions include madecassoside and optionally one or more additional skin active agents.

Depigmenting Agents

Nonlimiting examples of depigmenting agents include alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Agent

The term "anti-wrinkle agent" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Nonlimiting examples of anti-wrinkle agents include: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the skin tightening composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-—N-ethylcarboxamido adenosine (CGS-21680), N-ethylcarboxam ido-adenosine (NECA), the 5'(N-cyclopropyl)-carboxamidoadenosine, DPMA (PD 129.944) and metrifudil.

Miscellaneous ingredients can be included in the cosmetic composition, for example, in an amount of about 0.01 to about 10 wt. %, based on the total weight of the cosmetic composition. The total amount of the one or more miscellaneous ingredients may be about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, or about 1 to about 3 wt. %, based on the total weight of the cosmetic composition.

As already noted, skin active agents may be included as one or more of the miscellaneous ingredients. With respect to the total amount of skin active agents in the cosmetic compositions, if present, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, based on the total weight of the cosmetic composition.

pH

The cosmetic compositions of the instant disclosure typically have a pH of about 5.5 to about 8. In various embodiments, the pH of the cosmetic compositions have a pH of from 5.5 to about 7, about 5.5 to about 6.5, about 5.5 to about 6 to about 8, or about 6 to about 7. In various embodiments, the pH of the cosmetic compositions does not change by more than ±1 pH unit, ±0.5 pH units, ±0.3 pH units, or ±0.2 pH units, for at least 2 weeks, 4 weeks, and/or 8 weeks in storage at 4° C., 25° C., 37° C., and/or 45° C.

Stability

The cosmetic compositions of the instant disclosure are stable. For example, the cosmetic compositions do not visually phase separate or form visibly observable particulates for at least 2 weeks, 4 weeks, and/or 8 weeks in storage at 4° C., 25° C., 37° C., and/or 45° C.

In various embodiments, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C. In various embodiments, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

Viscosity

In general, the cosmetic compositions of the instant case have a viscosity of about 5,000 to about 200,000 Pa·s at 25° C., and shear rate of 1 s$^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 10,000 to about 100,000 Pa·s, about 10,000 to about 80,000 Pa·s, about 15,000 to about 200,000 Pa·s, about 15,000 to about 180,000 Pa·s, about 15,000 to about 150,000 Pa·s, about 15,000 to about 120,000 Pa·s, about 15,000 to about 100,000 Pa·s, about 15,000 to about 80,000 Pa·s, about 20,000 to about 200,000 Pa·s, about 20,000 to about 180,000 Pa·s, about 20,000 to about 150,000 Pa·s, about 20,000 to about 120,000 Pa·s, about 20,000 to about 100,000 Pa·s, about 20,000 to about 80,000 Pa·s, about 30,000 to about 200,000 Pa·s, about 30,000 to about 180,000 Pa·s, about 30,000 to about 150,000 Pa·s, about 30,000 to about 120,000 Pa·s, about 30,000 to about 100,000 Pa·s, about 30,000 to about 80,000 Pa·s, about 35,000 to about 200,000 Pa·s, about 35,000 to about 180,000 Pa·s, about 35,000 to about 150,000 Pa·s, about 35,000 to about 120,000 Pa·s, about 35,000 to about 100,000 Pa·s, about 35,000 to about 80,000 Pa·s, about 40,000 to about 200,000 Pa·s, about 40,000 to about 180,000 Pa·s, about 40,000 to bout 150,000 Pa·s, about 40,000 to about 120,000 Pa·s, about 40,000 to about 100,000 Pa·s, about 40,000 to about 80,000 Pa·s at 25° C., and shear rate of 1 s$^{-1}$ at 25° C.

The viscosity measurements can be carried out, for example, using a Brooksfield viscometer/rheometer using a t-bar spindle at a speed of 5, 10, 15, and/or 20 rpm. An RVDV-II+Pro Viscometer with RheocalcT software may be employed for automated instrument control and data acquisition. The test temperature is maintained at 25° C. by using a Brookfield TC-502P Programmable Refrigerated Bath. From its original container, a sample is transferred into a 120 mL glass jar and then tested.

Methods

The instant disclosure also relates to methods of treating skin. The methods include applying the cosmetic composition according to the instant disclosure. The cosmetic compositions are typically applied directly to the skin using the hand or a cloth. The skin may be optionally washed or rinsed prior to application. The method for treating the skin can be carried out once daily or may be carried out multiple times. For example, the method for treating skin may be carried out once daily, twice daily, weekly, bi-weekly for an extended period of time for 1, 2, 3, 4, 5, or 6 months. The methods may be methods for reinforcing or improving the natural lipid barrier of the skin; methods for treating dry and/or aging skin; methods for maintaining and/or improving moisture balance of the skin; and/or methods for improving the appearance of skin.

In certain embodiments, the method further comprises mixing a cosmetic composition of the instant disclosure with one or more additional cosmetic compositions prior to application to the skin. For example, the cosmetic composition of the instant disclosure can be mixed with one or more additional cosmetic compositions immediately prior to application to the skin, for example, the mixing may occur within 1 minute, 2 minutes, 5 minutes, 10 minutes, 15 minutes, or 30 minutes prior to application to the skin. In certain embodiments, the cosmetic compositions can be mixed in an individual's hands prior to applying the mixture to the skin, for example, the skin of the face.

The instant disclosure also relates to methods for stabilizing cosmetic composition containing high amounts of acetyl trifluoromethylphenyl valylglycine. This method comprises incorporating acetyl trifluoromethylphenyl valylglycine into the compositions of the instant disclosure. The amounts of acetyl trifluoromethylphenyl valylglycine that may be incorporated are the amounts set forth throughout the instant disclosure.

Kits

The cosmetic compositions of the instant disclosure may be provided in a kit, for example, a kit comprising an individually contained cosmetic composition according to the instant disclosure and one or more additional separately contained cosmetic compositions. In an embodiment, the one or more separately contained compositions may be an additional composition according to the instant disclosure or may be a different composition. The cosmetic compositions may be separately contained in different cartridges, which are included in a dispensing apparatus/device. In other words, the kit may be a dispensing apparatus/device comprising a plurality of cartridges in which the compositions are contained. The kit (or apparatus/device) may optionally dispense the cosmetic composition of the instant disclosure and separately dispense the one or more separately contained composition. In various embodiments, the compositions may be dispensed individually or concurrently, and may optionally be mixed (or not mixed) with each other prior to being dispensed. In an embodiment, the various compositions are not mixed with each other prior to being dispensed. Useful systems, cartridges, and dispensing apparatus/devices are disclosed in U.S. Pat. Nos. 9,968,177 and 9,808,071; US Patent Application Publication. Nos. 2021/0236390, 2021/0235849 and 2021/0236863; and in U.S. Ser. No. 17/162,555, which are all incorporated herein by reference in their entirety.

EMBODIMENTS

In some embodiments, the cosmetic composition comprises or consists of:
  (a) about 1 to about 5 wt. %, preferably about 2 to about 4 wt. %, more preferably about 2 to about 4 wt/% of acetyl trifluoromethylphenyl valylglycine;
  (b) about 10 to about 40 wt. %, more preferably about 10 to about 20 wt. %, and more preferably about 12 to about 18 wt. % of hydroxypropyl tetrahydropyrantriol;
  (c) about 2 to about 15 wt. %, preferably about 2 to about 8 wt. %, more preferably about 2 to about 5 wt. % of two or more, preferably three or more taurate copolymers, for example, chosen from acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof, preferably all three of acrylamide/sodium acryloyl dimethyl taurate copolymer, hydroxyethyl acrylate/sodium acryloyl dimethyl taurate copolymer, ammonium acryloyldimethyl taurate/VP copolymer;
  (d) about 0.5 to about 10 wt. %, preferably about 0.5 to about 8 wt. %, more preferably about 1 to about 5 wt. % of one or more fatty alcohols, preferably having from 10 to 30 carbon atoms, more preferably chosen from decyl alcohol, undecyl alcohol, dodecyl, myristyl, cetyl alcohol, stearyl alcohol, cetearyl alcohol, isostearyl alcohol, isocetyl alcohol, behenyl alcohol, oleyl alcohol, myricyl alcohol and a mixture thereof;
  (e) about 5 to about 25 wt. %, preferably about 5 to about 20 wt. %, more preferably about 5 to about 15 wt. % of one or more fatty compounds, for example, one or more fatty compounds chosen from fatty esters (such as isononyl isononanoate), polyolefins (such as petrolatum), waxes, squalane, squalene, hydrogenated polyisobutene, hydrogenated polydecene, polybutene, mineral oil, pentahydrosqualene, plant and/or vegetable oil, hydrocarbon-based oils (such as isohexadecane), and a mixture thereof, more preferably chosen from isohexadecane, isononyl isononanoate, squalene, soybean oil, and a mixture thereof;
  (f) about 0.1 to about 10 wt. %, preferably about 0.1 to about 5, even more preferably about 0.1 to about 3 wt. % of one or more nonionic emulsifiers, for example, chosen from alkanolam ides, sorbitan fatty esters (e.g., sorbitan isostearate and sorbitan oleate), ethoxylated sorbitan fatty esters (e.g., polysorbate-80), polyol esters, glyceryl esters, polyglucosides (e.g., cetearyl glucoside), glycerol ethers, oxyethylenated ethers, oxypropylenated ethers, and ethylene glycol polymers, preferably chosen from polysorbate 80, cetearyl glucoside, sorbitan isostearate, sorbitan oleate, mixtures thereof;
  (g) about 40 to about 80 wt. %, preferably about 40 to about 70 wt. %, more preferably about 45 to about 65 wt. % of water;
  (h) optionally, one or more water-soluble solvents, for example, one or more water-soluble solvents chosen glycerin, alcohols (for example, C1-30, C1-15, C1-10, or C1-4 alcohols), organic solvents, polyols (polyhydric alcohols), glycols (e.g., propylene glycol, butylene glycol, caprylyl glycol, etc.), and a mixture thereof, preferably one or more glycols, in particular propylene glycol, wherein if present, the one or more water-soluble solvents comprise about 0.1 to about 20 wt. %, preferably about 0.1 to about 15 wt. %, more preferably about 1 to about 15 wt. % of the cosmetic composition;
  (i) optionally, one or more thickening polymers that are different from the one or more taurate copolymers of (c), for example, chosen from polyacrylate, polymethacrylate, polyethylacrylate, polyacrylamide, poly C10-30 alkyl acrylate, and mixtures thereof, preferably poly C10-30 alkyl acrylate, wherein if present, the one or more thickening polymers comprise about 0.01 to about 5 wt. %, preferably about 0.05 to about 4 wt. %, more preferably about 0.1 to about 3 wt. % of the cosmetic composition;
  (j) optionally, one or more miscellaneous ingredients, for example, one or more miscellaneous ingredients chosen from miscellaneous emulsifiers/surfactants other than the nonionic emulsifiers of (f), preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, preferably wherein at least one of the one or more miscellaneous ingredients is a further skin active agent such as madecassoside, wherein if present, the one or more miscellaneous ingredients comprise about 0.01 to about 0.1 to about 10 wt. %, preferably about 0.1 to about 8 wt. %, more preferably about 1 to about 8 wt. % of the cosmetic composition;
  wherein the composition is an oil in water emulsion, preferably a gel emulsion, and all percentages by weight are based on the total weight of the cosmetic composition.

As noted above, in certain embodiments, it is preferable to include three or more taurate copolymers in the cosmetic composition. The three or more taurate copolymers may be ammonium acryloyldimethyl taurate/VP copolymer, acrylamide/sodium acryloyl dimethyl taurate copolymer, hydroxyethyl acrylate/sodium acryloyldimethyl taurate copolymer, preferably in the following amounts, based on the total weight of the cosmetic compositions:
  0.1 to 4 wt. %, preferably 0.5 to 3 wt. %, more preferably 0.6 to 2 wt. % of ammonium acryloyldimethyl taurate/VP copolymer,
  0.7 to 4 wt. %, preferably 0.7 to 3 wt. %, more preferably, 0.8 to 2 wt. % of acrylamide/sodium acryloyl dimethyl taurate copolymer, and 0.1 to about 4 wt. %, preferably 0.5 to 3 wt. %, more preferably 0.6 to 2 wt. % of hydroxyethyl acrylate/sodium acryloyldimethyl taurate copolymer.

In a particularly preferred embodiment, the cosmetic composition comprises:
  0.6 to 2 wt. % of ammonium acryloyldimethyl taurate/VP copolymer,
  0.8 to 2 wt. % of acrylamide/sodium acryloyl dimethyl taurate copolymer, and
  0.6 to 2 wt. % of hydroxyethyl acrylate/sodium acryloyldimethyl taurate copolymer.

The composition preferably has a pH of about 5.5 to about 8, preferably about 5.5 to about 7.5, more preferably about 5.5 to about 7.

The cosmetic compositions of the instant disclosure are stable. For example, the cosmetic compositions do not visually phase separate or form visibly observable particulates for at least 2 weeks, 4 weeks, and/or 8 weeks in storage at 4° C., 25° C., 37° C., and/or 45° C.

In various embodiments, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In various embodiments, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

The cosmetic compositions preferably have a viscosity of about 5,000 to about 200,000 Pa·s at 25° C., and shear rate of 1 s$^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 10,000 to about 100,000 Pa·s, about 10,000 to about 80,000 Pa·s, about 15,000 to about 200,000 Pa·s, about 15,000 to about 180,000 Pa·s, about 15,000 to about 150,000 Pa·s, about 15,000 to about 120,000 Pa·s, about 15,000 to about 100,000 Pa·s, about 15,000 to about 80,000 Pa·s, about 20,000 to about 200,000 Pa·s, about 20,000 to about 180,000 Pa·s, about 20,000 to about 150,000 Pa·s, about 20,000 to about 120,000 Pa·s, about 20,000 to about 100,000 Pa·s, about 20,000 to about 80,000 Pa·s, about 30,000 to about 200,000 Pa·s, about 30,000 to about 180,000 Pa·s, about 30,000 to about 150,000 Pa·s, about 30,000 to about 120,000 Pa·s, about 30,000 to about 100,000 Pa·s, about 30,000 to about 80,000 Pa·s, about 35,000 to about 200,000 Pa·s, about 35,000 to about 180,000 Pa·s, about 35,000 to about 150,000 Pa·s, about 35,000 to about 120,000 Pa·s, about 35,000 to about 100,000 Pa·s, about 35,000 to about 80,000 Pa·s, about 40,000 to about 200,000 Pa·s, about 40,000 to about 180,000 Pa·s, about 40,000 to bout 150,000 Pa·s, about 40,000 to about 120,000 Pa·s, about 40,000 to about 100,000 Pa·s, about 40,000 to about 80,000 Pa·s at 25° C., and shear rate of 1 s$^{-1}$ at 25° C.

In a preferred embodiment, the cosmetic composition comprises or consists of:
  (a) about 1 to about 5 wt. %, preferably about 2 to about 4 wt. %, more preferably about 2 to about 4 wt/% of acetyl trifluoromethylphenyl valylglycine;
  (b) about 10 to about 40 wt. %, more preferably about 10 to about 20 wt. %, and more preferably about 12 to about 18 wt. % of hydroxypropyl tetrahydropyrantriol;
  (c) about 2 to about 15 wt. %, preferably about 2 to about 8 wt. %, more preferably about 2 to about 5 wt. % of two or more, preferably three or more taurate copolymers, for example, chosen from acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof, preferably acrylamide/sodium acryloyl dimethyl taurate copolymer, hydroxyethyl acrylate/sodium acryloyl dimethyl taurate copolymer, and ammonium acryloyldimethyl taurate/VP copolymer;
  (d) about 0.5 to about 10 wt. %, preferably about 0.5 to about 8 wt. %, more preferably about 1 to about 5 wt. % of one or more fatty alcohols having from 10 to 30 carbon atoms, for example, one or more fatty alcohols chosen from decyl alcohol, undecyl alcohol, dodecyl, myristyl, cetyl alcohol, stearyl alcohol, cetearyl alcohol, isostearyl alcohol, isocetyl alcohol, behenyl alcohol, oleyl alcohol, myricyl alcohol and a mixture thereof, preferably comprising behenyl alcohol and cetearyl alcohol;
  (e) about 5 to about 25 wt. %, preferably about 5 to about 20 wt. %, more preferably about 5 to about 15 wt. % of one or more fatty compounds, for example, one or more fatty compounds chosen from fatty esters (such as isononyl isononanoate), polyolefins (such as petrolatum), waxes, squalane, squalene, hydrogenated polyisobutene, hydrogenated polydecene, polybutene, mineral oil, pentahydrosqualene, plant and/or vegetable oil, hydrocarbon-based oils (such as isohexadecane), and a mixture thereof, more preferably chosen from isohexadecane, isononyl isononanoate, squalene, soybean oil, and a mixture thereof;
  (f) about 0.1 to about 10 wt. %, preferably about 0.1 to about 5, even more preferably about 0.1 to about 3 wt. % of one or more nonionic emulsifiers, for example, chosen from sorbitan fatty esters (e.g., sorbitan isostearate and sorbitan oleate), ethoxylated sorbitan fatty esters (e.g., polysorbate-80), polyol esters, glyceryl esters, polyglucosides (e.g., cetearyl glucoside), preferably chosen from polysorbate 80, cetearyl glucoside, sorbitan isostearate, sorbitan oleate, mixtures thereof;
  (g) about 40 to about 80 wt. %, preferably about 40 to about 70 wt. %, more preferably about 45 to about 65 wt. % of water;
  (h) about 0.1 to about 20 wt. %, preferably about 0.1 to about 15 wt. %, more preferably about 1 to about 15 wt. % of one or more water-soluble solvents, for example, one or more water-soluble solvents chosen glycerin, alcohols (for example, C1-30, C1-15, C1-10, or C1-4 alcohols), organic solvents, polyols (polyhydric alcohols), glycols (e.g., propylene glycol, butylene glycol, caprylyl glycol, etc.), and a mixture thereof, preferably one or more glycols, preferably propylene glycol;
  (i) optionally, one or more thickening polymers that are different from the one or more taurate copolymers of (c), for example, chosen from polyacrylate, polymethacrylate, polyethylacrylate, polyacrylamide, poly C10-30 alkyl acrylate, and mixtures thereof, preferably poly C10-30 alkyl acrylate, wherein if present, the one or more thickening polymers comprise about 0.01 to about 5 wt. %, preferably about 0.05 to about 4 wt. %, more preferably about 0.1 to about 3 wt. % of the cosmetic composition;

(j) about 0.01 to about 0.1 to about 10 wt. %, preferably about 0.1 to about 8 wt. %, more preferably about 1 to about 8 wt. % of one or more miscellaneous ingredients, for example, one or more miscellaneous ingredients chosen from miscellaneous emulsifiers/surfactants other than the nonionic emulsifiers of (f), preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, preferably wherein at least one of the one or more miscellaneous ingredients is a further skin active agent, which is preferably madecassoside;

wherein the composition is an oil in water emulsion, preferably a gel emulsion and all percentages by weight are based on the total weight of the cosmetic composition.

As noted above, in some instance, three or more taurate copolymers may be included in the cosmetic composition. The three or more taurate copolymers may be ammonium acryloyldimethyl taurate/VP copolymer, acrylamide/sodium acryloyl dimethyl taurate copolymer, hydroxyethyl acrylate/sodium acryloyldimethyl taurate copolymer, preferably in the following amounts, based on the total weight of the cosmetic compositions:

0.1 to 4 wt. %, preferably 0.5 to 3 wt. %, more preferably 0.6 to 2 wt. % of ammonium acryloyldimethyl taurate/VP copolymer, 0.7 to 4 wt. %, preferably 0.7 to 3 wt. %, more preferably, 0.8 to 2 wt. % of acrylamide/sodium acryloyl dimethyl taurate copolymer, and 0.1 to about 4 wt. %, preferably 0.5 to 3 wt. %, more preferably 0.6 to 2 wt. % of hydroxyethyl acrylate/sodium acryloyldimethyl taurate copolymer.

In a preferred embodiment, the cosmetic composition comprises:

0.6 to 2 wt. % of ammonium acryloyldimethyl taurate/VP copolymer, 0.8 to 2 wt. % of acrylamide/sodium acryloyl dimethyl taurate copolymer, and 0.6 to 2 wt. % of hydroxyethyl acrylate/sodium acryloyldimethyl taurate copolymer.

The composition preferably has a pH of about 5.5 to about 8, preferably about 5.5 to about 7.5, more preferably about 5.5 to about 7.

The cosmetic compositions of the instant disclosure are stable. For example, the cosmetic compositions do not visually phase separate or form visibly observable particulates for at least 2 weeks, 4 weeks, and/or 8 weeks in storage at 4° C., 25° C., 37° C., and/or 45° C.

In various embodiments, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In various embodiments, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

The cosmetic compositions preferably have a viscosity of about 5,000 to about 200,000 Pa·s at 25° C., and shear rate of 1 s$^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 10,000 to about 100,000 Pa·s, about 10,000 to about 80,000 Pa·s, about 15,000 to about 200,000 Pa·s, about 15,000 to about 180,000 Pa·s, about 15,000 to about 150,000 Pa·s, about 15,000 to about 120,000 Pa·s, about 15,000 to about 100,000 Pa·s, about 15,000 to about 80,000 Pa·s, about 20,000 to about 200,000 Pa·s, about 20,000 to about 180,000 Pa·s, about 20,000 to about 150,000 Pa·s, about 20,000 to about 120,000 Pa·s, about 20,000 to about 100,000 Pa·s, about 20,000 to about 80,000 Pa·s, about 30,000 to about 200,000 Pa·s, about 30,000 to about 180,000 Pa·s, about 30,000 to about 150,000 Pa·s, about 30,000 to about 120,000 Pa·s, about 30,000 to about 100,000 Pa·s, about 30,000 to about 80,000 Pa·s, about 35,000 to about 200,000 Pa·s, about 35,000 to about 180,000 Pa·s, about 35,000 to about 150,000 Pa·s, about 35,000 to about 120,000 Pa·s, about 35,000 to about 100,000 Pa·s, about 35,000 to about 80,000 Pa·s, about 40,000 to about 200,000 Pa·s, about 40,000 to about 180,000 Pa·s, about 40,000 to bout 150,000 Pa·s, about 40,000 to about 120,000 Pa·s, about 40,000 to about 100,000 Pa·s, about 40,000 to about 80,000 Pa·s at 25° C., and shear rate of 1 s$^{-1}$ at 25° C.

EXAMPLES

As various changes could be made in the above-described methods without departing from the scope of the invention, it is intended that all matter contained in the above description and in the examples given below, shall be interpreted as illustrative and not in a limiting sense.

The following Examples are intended to be non-restrictive and explanatory only. The ingredient amounts in the compositions/formulas described below are expressed in % by weight, based on the total weight of the composition.

Example 1

| | | | Inventive | | | | | | Comparative | | |
|---|---|---|---|---|---|---|---|---|---|---|---|
| | | | A | B | C | D | E | F | C-1 | C-2 | C-3 |
| (a) | Active | ACETYL TRIFLUOROMETHYLPHENYL VALYLGLYCINE | 3.0 | 3.0 | 3.0 | 3.0 | 3.0 | 3.0 | 3.0 | 3.0 | 3.0 |
| (b) | Active | HYDROXYPROPYL TETRAHYDROPYRANTRIOL | 15.0 | 15.0 | 15.0 | 15.0 | 15.0 | 15.0 | 15.0 | 15.0 | 15.0 |
| (j) | Active (misc.) | MADECASSOSIDE | 0.9 | 0.9 | 0.9 | 0.9 | 0.9 | 0.9 | 0.9 | 0.9 | 0.9 |
| (c) | Taurate Copolymer | AMMONIUM ACRYLOYLDIMETHYLTAURATE/VP COPOLYMER | 1.2 | 0.7 | 0.7 | 1.0 | 1.2 | 0.7 | 1.2 | 0.7 | 0.7 |
| | | ACRYLAMIDE/SODIUM | 1.0 | 1.0 | 0.8 | 1.0 | 1.0 | 1.0 | 0.5 | 1.0 | 0.6 |

-continued

|  |  |  | Inventive | | | | | | Comparative | | |
| --- | --- | --- | --- | --- | --- | --- | --- | --- | --- | --- | --- |
|  |  |  | A | B | C | D | E | F | C-1 | C-2 | C-3 |
|  |  | ACRYLOYLDIMETHYLTAURATE COPOLYMER |  |  |  |  |  |  |  |  |  |
|  |  | HYDROXYETHYL ACRYLATE/SODIUM ACRYLOYLDIMETHYL TAURATE COPOLYMER | 0.7 | 0.7 | 0.7 | 0.7 | 0.7 | 0.7 | 0.7 | — | 0.7 |
| (d) | Fatty Alcohol | BEHENYL ALCOHOL and CETEARYL ALCOHOL | 1.8 | 1.8 | 1.8 | 1.8 | 1.8 | 1.8 | 1.8 | 1.8 | 1.8 |
| (i) | Thickening Polymer | POLY C10-30 ALKYL ACRYLATE | 0.5 | 0.5 | — | 0.5 | 0.5 | 0.5 | 0.5 | 0.5 | — |
| (e) | Fatty Compound | ISOHEXADECANE, ISONONYL ISONONANOATE, SQUALANE, AND/OR GLYCINE SOJA (SOYBEAN) OIL | 9.5 | 9.5 | 9.5 | 9.5 | 9.5 | 9.5 | 9.5 | 9.5 | 9.5 |
| (f) | Nonionic Emulsifier | POLYSORBATE 80, CETEARYL GLUCOSIDE, SORBITAN ISOSTEARATE, AND/OR SORBITAN OLEATE | 0.5 | 0.5 | 0.4 | 0.5 | 0.5 | 0.5 | 0.4 | 0.5 | 0.4 |
| (h) | Solvent | PROPYLENE GLYCOL | 10.7 | 1.7 | 1.7 | 1.7 | 1.7 | 1.7 | 10.7 | 1.7 | 1.7 |
| (j) | Miscellaneous emulsifers/surfactants, salts, preservatives, pH adjusters, fragrances, colorants, chelants, and/or extracts, etc. | | ≤4 | ≤4 | ≤4 | ≤4 | ≤4 | ≤4 | ≤4 | ≤4 | ≤4 |
| (g) | Water | WATER | 54.0 | 63.6 | 64.3 | 63.2 | 63.0 | 63.4 | 55.0 | 64.4 | 64.6 |
|  |  | Stable | Y | Y | Y | Y | Y | Y | N | N | N |

Example 2

Comparative Compositions

|  |  |  | C-4 | C-5 | C-6 |
| --- | --- | --- | --- | --- | --- |
| (a) | Active | ACETYL TRIFLUOROMETHYLPHENYL VALYLGLYCINE | 3.0 | 3.0 | 3.0 |
| (b) | Active | HYDROXYPROPYL TETRAHYDROPYRANTRIOL |  | 15.0 | 15.0 |
| (c) | Taurate Copolymer | AMMONIUM ACRYLOYLDIMETHYLTAURATE/ VP COPOLYMER |  | 1.5 |  |
| (d) | Fatty Alcohol | BEHENYL ALCOHOL and CETEARYL ALCOHOL |  |  | 0.8 |
|  | Thickening Agent | SODIUM POLYACRYLATE | 1.3 | 0.4 | 0.4 |
| (e) | Fatty Compound | ISONONYL ISONONANOATE, CETEARYL ETHYLHEXANOATE, AND/OR CAPRYLIC/ CAPRIC TRIGLYCERIDE | 3 | 2.7 | 2.7 2.7 |
|  | Silicone | DIMETHICONE |  | 0.5 | 0.5 |
| (f) | Nonionic Emulsifier | CETEARYL GLUCOSIDE |  |  | 0.2 |
| (h) | WS Solvent | PROPYLENE GLYCOL AND/OR GLYCERIN | 8 | 10.7 | 10.7 |
| (j) | Miscellaneous emulsifers/surfactants, Emolliants, Salts, Preservatives, pH Adjusters, Fragrances, Colorants, Chelants, and/or Extracts, Etc. | | ≤4 | ≤4 | ≤4 |
| (g) | Water |  | 77 | 57 | 58 |
|  |  | Stable | N | N | N |

Example 3

Stability Testing

The compositions of Example 1 and Example 2 were subjected to stability studies and visually evaluated for phase separation and assessed under a microscope for particulate formation. The compositions were assessed upon initial manufacture of the composition (To). The compositions were again evaluated after 10 days of freeze-thaw testing. The compositions were placed in a stability chamber and subjected to temperature fluctuation at 12-hour intervals. For 12 hours, the compositions were held at −20° C. For the next 12 hours, the compositions were held at 25° C. The cycle was repeated 10 times (for 10 days). Separately, the compositions of Example 1 and Example 2 were evaluated after 2 weeks in storage at 4° C., 25° C., 37° C., and 45° C., 4 weeks (1 month) in storage at 4° C., 25° C., 37° C., and 45° C., and again at 8 weeks (2 months) in storage at 4° C., 25° C., 37° C., and 45° C. and visually evaluated for phase separation and assessed under a microscope for particulate formation.

The inventive compositions were deemed stable ("Y") (yes) because they did not visually phase separate and did not form particulates. The Comparative Compositions (C-1 through C-6), however, phase separated and formed particulates. Therefore, the Comparative Compositions were deemed not stable ("N") (no).

The data shows, among other things, the importance of including at least two taurate copolymers in an amount of at least 2 wt. %, based on the total weight of the composition.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

Definitions

As used herein, a "gel emulsion" is also referred to in the art as "emulsion gel." A gel emulsion is an oil in water emulsion, which is a composite structure of oil droplets within a gel matrix. They can be categorized as emulsion-filled gels and emulsion particulate gels.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements chosen from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting. Appropriate counterions for the components described herein are known in the art.

The expression "one or more" means "at least one" and thus includes individual components as well as mixtures/combinations.

The term "plurality" means "more than one" or "two or more."

An "alkyl radical" is a linear or branched saturated hydrocarbon-based group, particularly $C_1$-$C_8$, more particularly $C_1$-$C_6$, preferably $C_1$-$C_4$ such as methyl, ethyl, isopropyl and tert-butyl;

An "alkoxy radical" is a alkyl-oxy wherein alkyl is as described herein before;

An "alkenyl radical" is a linear or branched unsaturated hydrocarbon-based group, particularly $C_2$-$C_8$, more particularly $C_2$-$C_6$, preferably $C_2$-$C_4$ such as ethylenyl, propylenyl;

An "alkylene radical" is a linear or branched divalent saturated $C_1$-$C_8$, in particular $C_1$-$C_6$, preferably $C_1$-$C_4$ hydrocarbon-based group such as methylene, ethylene or propylene.

Some of the various categories of components identified for the cosmetic compositions may overlap. In such cases where overlap may exist and the composition/product includes two overlapping components (or more than two overlapping components), an overlapping component does not represent more than one component. As an example, a fatty acid may be considered both a "non-triglyceride and non-aromatic fatty emollient" and a "surfactant/emulsifier." If a particular composition/product includes both a non-triglyceride and non-aromatic fatty emollient component and an surfactant/emulsifier component, a single type of fatty acid can serve as only a non-triglyceride and non-aromatic fatty emollient or a surfactant/emulsifier (a single fatty acid does not serve as both the non-triglyceride and non-aromatic fatty emollient component and the surfactant/emulsifier component).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions may be modified with the term "about," whether or not expressly stated.

Additionally, all numbers are intended to represent exact values as additional embodiments, whether or not modified by the term "about." For example, "an amount of about 1%" can be modified to refer to exactly 1%. As a further example, "an amount of 1%" can be modified to refer to "about 1%." Unless otherwise indicated, the term "about" is understood to encompass a range of +/−10% from the stated number. However, in some embodiments, the term may be defined to encompass narrower ranges, for example, +/−1%, 2%, 3%, 4%, 5%, 6%, 7%, 8%, 9%, and 10% from the stated number.

The term "surfactants" and "emulsifiers" include salts of the surfactants and emulsifiers even if not explicitly stated. In other words, whenever the disclosure refers to a surfactant or emulsifier, it is intended that salts are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants and emulsifiers. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the composition (provided that an amount of less than 2% by weight does not materially affect the basic and novel characteristics of the claimed invention). Similarly, a composition "substantially free" or "essentially free" of a stated material may include less than 1.5 wt. %, less than 1 wt. %, less than 0.5 wt. %, less than 0.1 wt. %, less than 0.05 wt. %, or less than 0.01 wt. %, or none of the specified material. The term "substantially free" or "essentially free" as used herein may also mean that the specific material is not added to the composition but may still be present in a raw material that is included in the composition.

Furthermore, all components that are positively set forth in the instant disclosure may be negatively excluded from the claims, e.g., a claimed composition may be "free," "essentially free" (or "substantially free") of one or more components that are positively set forth in the instant disclosure. As an example, Silicones can optionally be included in the cosmetic compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, cosmetic compositions of the instant case can be free or essentially free from dimethicones, amomdimethicones, dimethiconols, cyclosiloxanes, siloxanes, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:
1. A cosmetic composition comprising:
(a) about 1 to about 5 wt. % of acetyl trifluoromethylphenyl valylglycine;
(b) about 12 to about 20 wt. % of hydroxypropyl tetrahydropyrantriol;
(c) about 2.5 to about 5 wt. % of two or more taurate copolymers, wherein one of the two or more taurate copolymers is hydroxyethyl acrylate/sodium acryloyl dimethyl taurate copolymer and additional taurate copolymers are chosen from acrylamide/sodium acryloyl dimethyl taurate copolymer, ammonium acryloyldimethyl taurate/vinylpyrrolidone (VP) copolymer, and sodium acrylate/sodium acryloyl dimethyl taurate copolymer;
(d) about 0.5 to about 10 wt. % of one or more fatty alcohols;
(e) about 5 to about 25 wt. % of one or more fatty compounds;
(f) about 0.1 to about 10 wt. % of one or more nonionic emulsifiers; and
(g) water;
wherein the composition is an oil in water emulsion
the composition does not visually phase separate or form particulates for at least 10 cycles of freeze-thaw testing, wherein a cycle of freeze-thaw testing comprises placing the cosmetic composition in a stability chamber and subjecting it to temperature fluctuation at 12-hour intervals, for a first interval of 12 hours at −20° C. followed by a second interval of 12 hours at 25° C., and all percentages by weight are based on the total weight of the cosmetic composition.

2. The composition of claim 1 comprising three or more taurate copolymers.

3. The composition of claim 1, wherein the one or more fatty alcohols are chosen from C6-C20 fatty alcohols.

4. The composition of claim 3, wherein the one or more fatty alcohols are chosen from decyl alcohol, undecyl alcohol, dodecyl alcohol, myristyl alcohol, cetyl alcohol, stearyl alcohol, isostearyl alcohol, isocetyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof.

5. The composition of claim 1, wherein the one or more fatty compounds are chosen from fatty esters (isononyl isononanoate), polyolefins (petrolatum), waxes, squalane, squalene, hydrogenated polyisobutene, hydrogenated polydecene, polybutene, mineral oil, pentahydrosqualene, plant and/or vegetable oil, hydrocarbon-based oils (isohexadecane), and a mixture thereof.

6. The composition of claim 1, wherein the one or more nonionic emulsifiers are chosen from alkanolamides, sorbitan fatty esters, ethoxylated sorbitan fatty esters, polysorbate-80, polyol esters, glyceryl esters, polyglucosides, glycerol ethers, oxyethylenated ethers, oxypropylenated ethers, and ethylene glycol polymers.

7. The composition of claim 1 comprising about 35 to about 85 wt. % of water.

8. The composition of claim 1, further comprising:
(h) one or more water-soluble solvents.

9. The composition of claim 8 comprising about 0.1 to about 20 wt. % of the one or more water-soluble solvents.

10. The composition of claim 8, wherein the one or more water-soluble solvents are chosen from glycerin, monoalcohols, polyols, glycols, and a mixture thereof.

11. The composition of claim 1, further comprising:
(i) one or more additional skin active ingredients.

12. The composition of claim 11 comprising about 0.01 to about 5 wt. % of the one or more additional skin active ingredients.

13. The composition of claim 11, wherein the one or more additional skin active ingredients are chosen from madecassoside, a moisturizing agent, a depigmenting agent, an anti-wrinkle agent, a skin active agent for oily skin, an antioxidant, a flavonoid, a vitamin, a skin whitening agent, and a mixture thereof.

14. The composition of claim 1 having a pH of about 5.5 to about 7.5.

15. The composition of claim 1 having a viscosity of about 20,000 to about 80,000 Pa·s at 25° C., and shear rate of 1 s-1 at 25° C.

16. A cosmetic composition comprising
(a) about 1 to about 5 wt. % of acetyl trifluoromethylphenyl valylglycine;
(b) about 12 to about 20 wt. % of hydroxypropyl tetrahydropyrantriol;
(c) about 2.5 to about 5 wt. % of two or more tau rate copolymers, wherein one of the two or more taurate copolymers is hydroxyethyl acrylate/sodium acryloyl dimethyl taurate copolymer in an amount of at least 0.7 wt. %, and additional taurate copolymers are chosen from acrylamide/sodium acryloyl dimethyl taurate copolymer, ammonium acryloyldimethyl taurate/VP copolymer, and sodium acrylate/sodium acryloyl dimethyl taurate copolymer;

(d) about 0.5 to about 10 wt. % of one or more fatty alcohols chosen from behenyl alcohol and cetearyl alcohol;

(e) about 5 to about 20 wt. % of one or more fatty compounds chosen from isohexadecane, isononyl isononanoate, squalene, and *glycine soja* oil, soybean oil;

(f) about 0.1 to about 10 wt. % of one or more nonionic emulsifiers; and (g) about 35 to about 75 wt. % of water;

(h) about 0.1 to about 15 wt. % of one or more water-soluble solvents chosen from glycerin, mono-alcohols, polyols, polyhydric alcohols, glycols, and a mixture thereof; and (i) optionally, one or more additional skin active ingredients; wherein the composition is an oil in water emulsion, the composition does not visually phase separate or form particulates for at least 10 cycles of freeze-thaw testing, wherein a cycle of freeze-thaw testing comprises placing the cosmetic composition in a stability chamber and subjecting it to temperature fluctuation at 12-hour intervals, for a first interval of 12 hours at −20° C. followed by a second interval of 12 hours at 25° C., and all percentages by weight are based on the total weight of the cosmetic composition.

17. A kit comprising the cosmetic composition of claim 1 and one or more additional skin treatment compositions, wherein the cosmetic composition and each of the one or more skin treatment compositions are separately contained.

18. A method for treating skin comprising applying the cosmetic composition of any one of claim 1 to the skin.

19. The cosmetic composition of claim 1, further comprising:

(h) about 0.1 to about 15 wt. % of one or more water-soluble solvents chosen from glycerin, mono-alcohols, polyols, polyhydric alcohols, glycols, and a mixture thereof;

(i) optionally, one or more additional skin active ingredients; and (j) one or more thickening polymers chosen from polyacrylate, polymethacrylate, polyethylacrylate, polyacrylamide, and poly C10-30 alkyl acrylate.

20. The cosmetic composition of claim 19 comprising three or more taurate copolymers, wherein the three or more taurate copolymers comprise:

from 0.6 to 2 wt. % of ammonium acryloyldimethyl taurate/VP copolymer, from 0.8 to 2 wt. % of acrylamide/sodium acryloyl dimethyl taurate copolymer, and from 0.6 to 2 wt. % of hydroxyethyl acrylate/sodium acryloyldimethyl taurate copolymer.

* * * * *